Figure 1:
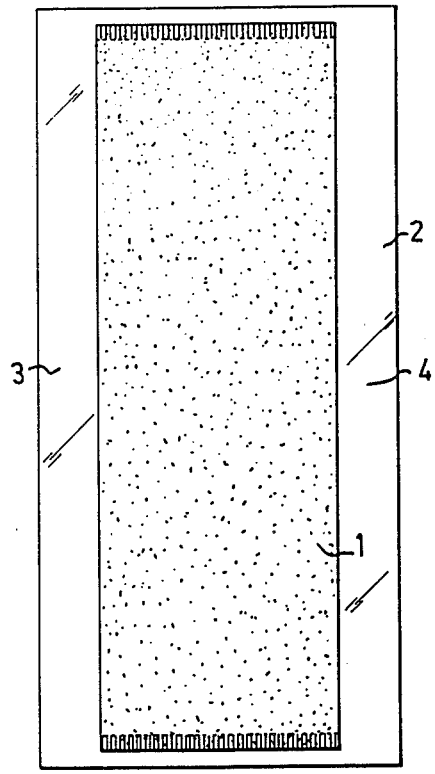

United States Patent [19]

Runeman

[11] Patent Number: 4,710,188
[45] Date of Patent: Dec. 1, 1987

[54] INCONTINENCE PROTECTOR AND A METHOD FOR ITS MANUFACTURE

[75] Inventor: Bo Runeman, Göteborg, Sweden
[73] Assignee: Molnlycke AB, Gothenburg, Sweden
[21] Appl. No.: 825,913
[22] Filed: Feb. 4, 1986
[30] Foreign Application Priority Data
Feb. 4, 1985 [SE] Sweden .............................. 8500492
[51] Int. Cl.⁴ .............................................. A61F 5/44
[52] U.S. Cl. .................. 604/385 R; 604/358
[58] Field of Search .............. 604/385, 358, 347, 349, 604/351–353

[56] References Cited

U.S. PATENT DOCUMENTS

| | | | |
|---|---|---|---|
| 3,707,969 | 1/1973 | Sanford | 604/347 |
| 3,968,799 | 7/1976 | Schrading | 604/385.1 |
| 4,453,938 | 6/1984 | Brendling | 604/349 |
| 4,590,931 | 5/1986 | Kidwell, Jr. | 604/349 |

FOREIGN PATENT DOCUMENTS

| | | | |
|---|---|---|---|
| 722427 | 11/1965 | Canada | 604/347 |
| 3036664 | 4/1982 | Fed. Rep. of Germany . | |
| 2463610 | 2/1981 | France . | |
| 2568469 | 8/1984 | France | 604/347 |
| 426206 | 12/1982 | Sweden . | |
| 8303663 | 6/1983 | Sweden . | |

Primary Examiner—C. Fred Rosenbaum
Assistant Examiner—Sherri E. Vinyard
Attorney, Agent, or Firm—Young & Thompson

[57] ABSTRACT

An incontinence protector for men including an absorbent layer of substantially rectangular shape which is folded together, and a liquid impermeable casing enclosing the two planar outsides of the absorbent layer, the folding edge and an edge situated close thereto, as well as a method of manufacturing such an incontinence protector.

2 Claims, 5 Drawing Figures

INCONTINENCE PROTECTOR AND A METHOD FOR ITS MANUFACTURE

The present invention relates to an incontinence protector for male users and is intended to serve as a container-like closure accommodating the penis and scrotum. The invention also relates to a method of manufacturing such an incontinence protector.

Incontinence protectors used up to now generally have the form of conventional diapers of substantially planar design and, for example, rectangular shape. Because of their purpose of absorbing urine as well as feces, however, diapers are not useful for individuals needing only a urine collecting incontinence protector. In fact, the absorbing portion of the diaper must have a certain width and a certain thickness for providing a satisfactory absorption capacity. The result is that the diaper will occupy a correspondingly large space between the legs, causing thereby an unpleasant feeling such as chafing to the wearer of the diaper. Furthermore, there is a great risk of urine leaking out at the diaper edges when the diaper becomes saturated and is compressed between the legs of the user.

Voluminous, ill-adapted diapers are unacceptable for men suffering from incontinence but being otherwise undisabled. In addition to the discomfort caused by wearing clumsy diapers, there is also no space allowed therefor in normal clothing, which will lead to mental suffering.

The technique of designing an incontinence protector as a relatively small container is known per se, said container serving the purpose of enclosing solely the user's penis and consisting of an outer layer of liquid impermeable material and an absorbent material disposed inside it. This kind of protection, however, fulfills its function only with men whose penis is of normal size, enabling it to be placed in the container and remaining continually enclosed therein. Such protectors are furthermore suitable only for slightly incontinent users, i.e. for individuals leaking only insignificant amounts of urine dropwise.

Moreover, specific problems arise in connection with the design of suitable incontinence protectors for elderly men having such a diminished penis that it is too small to be placed in a tubular casing.

As in Swedish Patent Specification No. 426 206, attempts have been made to overcome the problem of retaining a container-like protective device on users having a small or diminished penis by designing said device for a close fit to the body within the region of the penis root, trying in this manner to accomplish a more secure retention of the container.

The protective device according to said publication has a flat tubular portion with two pairs of opposed edges. This piece of tube has substantially the form of a parallelogram with three closed edges, whereas the fourth edge is left open. There is thus obtained at the opening one acute and one obtuse corner. During use of the device, the acute corner should be turned upwards and the obtuse corner be turned downwards. In contrast to other prior art urine collectors having their opening edge located at right angles to the longitudinal direction of the container, the side eges of the opening in the device according to said publication will extend obliquely upwards on the sides of the penis root, this arrangement being alleged to afford a fairly safe attachment keeping the protective device fixed even in the event of a rather small-sized penis.

The incontinence protector described above and known from the aforesaid publication does not fully satisfy its function and can easily slip away from its predetermined position. A serious disadvantage is that these protectors are relatively rigid and do not conform to the bodily shape of the user. Also, their capacity is sufficient only for dropwise incontinent users.

The latter applies to all prior art incontinence protectors consisting of a collector to be utilized for the accommodation of penis alone. For heavily incontinent users, such container-like absorption bodies intended to accommodate penis alone will fail to serve their purpose. The quantities of fluid, amounting sometimes to several deciliters, will demand a high absorption capacity involving large collectors which, when applied around the penis alone, will appear much too awkward.

Furthermore, the Swedish Patent Application No. 8303663-2 teaches an incontinence protector for men which is bodily adapted and which encloses penis as well as scrotum. Said protector has a front portion, a rear portion, and a uniting mid-portion which is narrower than said interconnected front and rear portions and which serves as the bottom of the container-like protector. Since the protector is designed to accommodate both penis and scrotum of the user, the rear portion thereof is provided with a slit or cut-out extending from the end edge. The wings on the rear portion, formed by the slit or cut-out on either slit side, are intended to be attached to the body underneath the scrotum. In this manner the protector will be more securely retained even if the user's penis is small, enabling simultaneously the protector to provide a sufficient absorption capacity without being clumsy.

There is an essential drawback associated with the protector designed in accordance with the Swedish Patent Application No. 8303663-2 in that its manufacture is complicated. A further drawback is the irregular shape of such protectors, which makes them difficult to pack.

With the present invention, however, there is achieved an incontinence protector which is well-adapted to the male body and which simultaneously allows manufacturing and packing in a most simple manner.

An incontinence protector in accordance with the invention is primarily distinguished by comprising an absorbent layer of a substantially rectangular basic shape and which is applied in a folded condition to constitute the protector, as well as a liquid impermeable casing affixed to the absorbent layer while enclosing the two planar outer surfaces of the folded absorbent layer, the folding edge of the absorbent layer and an edge situated close to the folding edge, said casing leaving the two remaining edges open into the space between the folded absorbent layer, whereby the protector is brought to its state of use by folding the shorter one of the two edges sealed by the casing against the other sealed edge, the protector in this state forming a more or less conical container.

The invention is an important advance within its field of products. As a matter of fact, it is possible according to the invention to create an incontinence protector out of a rectangular absorption body such as, for example, a conventional rectangular diaper and a plastic film applied to one of its surfaces. This is done by merely folding the absorption body with the plastic film and sealing it along one side in its folded state. When put on, the protector is simply folded to form a bodily conformed protection. The adaptation to the body can then be further improved by providing the protector along its longest open edge with an elastic member applied in a prestretched state and intended to form a softly rounded-off opening portion tightly sealing around the penis root during use of the protector.

Figure 2:
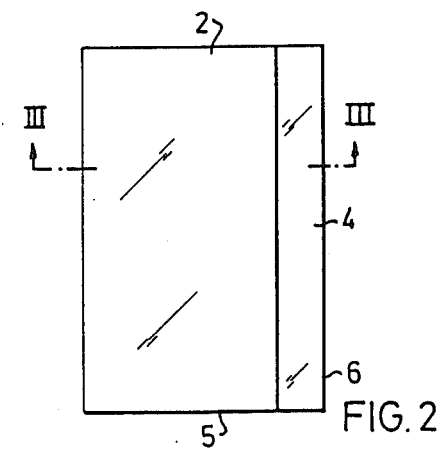
Figure 3:
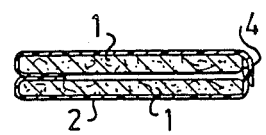
Figure 4:
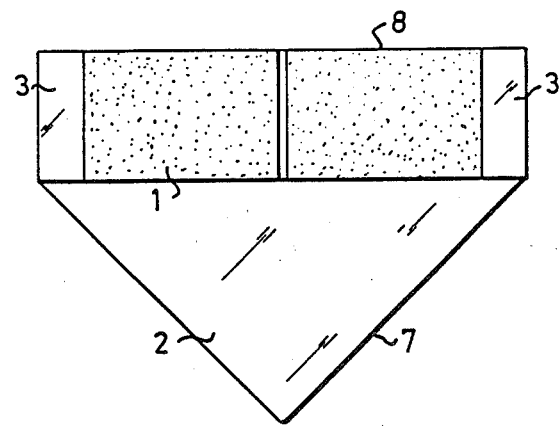

The invention will be described in more detail below with reference to two exemplary embodiments shown in the accompanying drawings, of which FIG. 1 is a plan view of the main components forming an incontinence protector according to the invention, FIG. 2 is a plan view of a protector formed of the components shown in FIG. 1, FIG. 3 is a section taken along the line III—III in FIG. 2, FIG. 4 shows the incontinence protector according to FIG. 2 folded out to its state of use, and FIG. 5 finally is a view corresponding to that of FIG. 4 and showing an incontinence protector according to the invention, provided with a softly rounded-off opening portion.

FIG. 1 illustrates a rectangular diaper 1 consisting of a cellulose absorption body surrounded by a wrap made of fiber fabric. The absorption body is applied at the center of a plastic film 2 with side edge portions 3,4 extending laterally beyond the absorption body and with its mid-portion suitably glued to the absorption body by means of hot melt.

For creating the incontinence protector, the edge portion 3 is first bent in over the absorption body and is glued thereto, whereafter the absorption body and the plastic film are folded together. The bent-together, overlapping parts of the edge portion 4 are united by gluing or welding, whereafter these united parts are bent around the edge portion of the folded absorption body and are fixed by gluing in this position. The incontinence protector thus obtained is illustrated in FIGS. 2 and 3.

In its condition shown in FIG. 2 the protector has uniform thickness, enabling in this manner a number of protectors to be piled on top of one another for producing a multi-piece package.

The incontinence protector according to FIG. 2 is easily brought to its state of use by pressing in the folding edge 5 against the other closed edge 6. In this manner the incontinence protector will be opened to its state of use as shown in FIG. 4, the bottom portion of the folded product thereby forming a more or less conical container 7 and the top portion forming a splash guard 8.

The more or less conical bottom portion may extend into the user's crotch without the risk of chafing, whereas the splash guard 8 extends up over the abdomen. Due to the design of the incontinence protector, the incorporated absorption body can have very thick dimensions without becoming voluminous and uncomfortable to wear.

Figure 5:
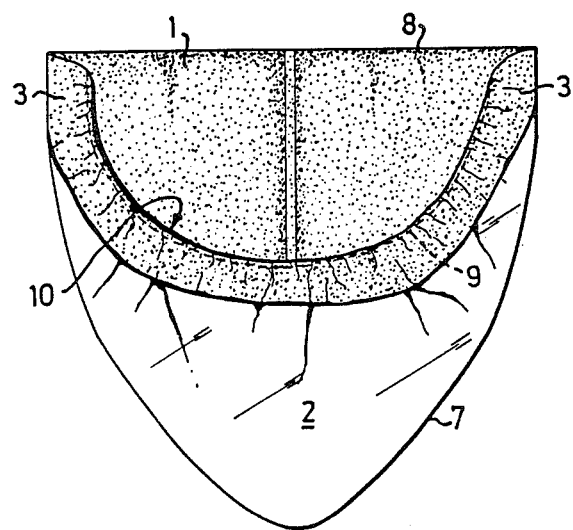

As illustrated in FIG. 5 showing another embodiment of a protector made in accordance with the invention, a softly rounded-off opening portion 10 is obtained if a prestretched elastic thread or elastic band 9 is affixed to the one longitudinally extending side edge portion 3 running beyond the absorption body, which portion is then folded in over said thread or band in order to form the opening edge facing the penis root during use of the protector.

With regard to the choice of rectangular size and length in relation to the width of the absorption body and the plastic film, the size and extent of the more or less conical container and the splash guard can be arbitrarily selected.

For users having a diminished penis it is particularly vital that the splash guard 8 is lengthy while extending well up over the abdomen.

The inventive incontinence protector is preferably combined with an elastic pant keeping the protector fixed in position.

The invention is not restricted to the embodiments described above, but a plurality of modifications are conceivable within the scope of the following claims.

The absorption body material need not necessarily be fluff pulp but could as well be some other material. If a thin protector is desired, the absorption body could be made of a material bonded in sheet form for example, possibly including a highly absorbent material bonded therein.

If desired, the point of the conical container can be made less sharp by folding the absorption body somewhat obliquely.

The protector described and illustrated above comprises a rectangular absorption body and a corresponding plastic layer. If desired, the more or less conical container can be made broader at the top in relation to the dimensions of the splash guard by letting portions of the oblong absorption body project laterally in one direction from the purely rectangular shape at or in the vicinity of the oblong blank center, the folded blank thus having its greatest width in an area close to the folding line.

I claim:

1. A method of manufacturing an incontinence protector for men, comprising securing together a rectangular absorbent layer and a rectangular liquid impermeable layer with an edge of the impermeable layer extending beyond the adjacent edge of the absorbent layer, folding the secured together layers double with the impermeable layer on the outside about a fold line perpendicular to said edge of the impermeable layer, thereby to bring two lengths of said edge of the impermeable layer into parallel juxtaposed position, and securing together only said juxtaposed lengths of said edge of the impermeable layer along a line of securement that is perpendicular to said fold line and that meets said fold line at one end of said fold line.

2. A method as claimed in claim 1, and securing to said impermeable layer a prestretched elongated elastic member that extends lengthwise along the edge of said impermeable layer that is opposite the secured edge of the impermeable layer.

* * * * *